United States Patent [19]

Komatsu et al.

[11] Patent Number: 4,592,967
[45] Date of Patent: Jun. 3, 1986

[54] GAS SENSOR OF MIXED OXIDES

[75] Inventors: Koji Komatsu, Toyonaka; Sai Sakai, Osaka, both of Japan

[73] Assignee: New Cosmos Electric Co., Ltd, Japan

[21] Appl. No.: 575,629

[22] Filed: Feb. 24, 1984

[30] Foreign Application Priority Data

Feb. 3, 1983 [JP] Japan .................................. 58-15464
Jul. 23, 1983 [JP] Japan .......................... 58-113726[U]

[51] Int. Cl.$^4$ ............................................... B32B 9/00
[52] U.S. Cl. ..................................... 428/697; 338/34; 340/634; 428/699
[58] Field of Search ........................ 338/34; 340/634; 428/312.2, 312.6, 312.8, 697, 699

[56] References Cited

U.S. PATENT DOCUMENTS 4,397,888 8/1983 Yannopoulos et al. ............. 340/634
4,507,643 3/1985 Sunano et al. ........................ 338/34

Primary Examiner—William J. Van Balen
Attorney, Agent, or Firm—Jones, Tullar & Cooper

[57] ABSTRACT

A gas sensor comprising a sintered piece composed of tin oxide, at least one of lanthanide oxides and at least one of IVa group element oxides. The sintered piece may be covered or coated with a porous layer of a ceramic material such as silica, alumina or silica-alumina.

5 Claims, No Drawings

GAS SENSOR OF MIXED OXIDES

BACKGROUND OF THE INVENTION

This invention relates to a gas sensor of the sintered tin oxide ($SnO_2$) type having improved stability with respect to the passage of time, and more particularly to a gas sensor improved not only in respect of stability with respect to the passage of time but in respect of poison resistance against organic silicone and the like.

Conventional sensors used for detecting combustible gases such as methane gas, liquefied propane gas, town gas, hydrogen and carbon monoxide include catalytic oxidation type sensors, the latter utilizing metal oxides such as tin oxide, ferric oxide, and the like. Tin oxide semiconductor type sensors generally comprise a pair of electrodes and a sintered piece provided therebetween and containing tin oxide as a main component, the sintered piece also containing an electric conductance improver such as $SnCl_2$, a heat resisting insulator such as silica, alumina or silica-alumina, and in some cases a precious metal catalyzer such as platinum, palladium, rhodium or the like. When such a gas sensor contacts a combustible gas and the sintered semiconductor absorbs the gas, its electric conductance increases sharply. When the combustible gas is no longer present the sintered semiconductor desorbs the gas therefrom and restores the electric conductance to an original value. To carry out the adsorption and desorption quickly, the sintered semiconductor which is the gas sensing unit is heated directly or indirectly and, generally, is constantly maintained at 300°–450° C.

Since the gas sensor is in use constantly energized to heat the sintered semiconductor portion to 300°–450° C. as noted above, the continuing high temperature, especially at times of high humidity, brings about changes in a surfacial fine structure of the sintered semiconductor and an increase in the electrical conductance of the sintered semiconductor. Therefore, depending on the lapse of use period and on use surroundings, an alarm may be given even when gas concentration is below a predetermined value at which the gas sensor is set to give an alarm. This has been a great problem of conventional alarm devices.

In recent years organic silicone materials such as silicone putty, silicone rubber, silicone oil and so forth have become widely used in construction. However, such organic silicone materials contain volatile oligomer which vaporizes into the ambient air. This silicone vapor adheres to the gas sensor surface and causes a problem of catalytic poisoning which results in deterioration of the gas sensor with the passage of time. A town gas alarm comprising the sintered piece of tin oxide will, when organic silicone adheres thereto, have an increased sinsitivity to miscellaneous gases such as of alcohol and give false alarms. At integrated circuit manufacturing plants silicone putty is extensively used on walls of clean rooms to maintain airtightness. Some semiconductor type chlorine gas alarms installed in such places have nil sensitivity in one month and in the case of catalytic oxidation type gas alarms the sensitivity sometimes is lost in one week. In either of the above cases the cause is considered to be organic silicone molecules having strong adhering activity which cover the activity points on the surface of the gas sensor and thus prevent the gas from being adsorbed thereto.

SUMMARY OF THE INVENTION

This invention has been made having regard to the above state of the art. Therefore, the primary object of this invention is to provide a gas sensor with tin oxide containing a lanthanide oxide and an oxide of the IVa group element, i.e. titanium (Ti), zirconium (Zr), hafnium (Hf) or thorium (Th), each in a range of 0.01–20 mol %, thereby to keep suitable electric conductance, its conductance and gas sensitivity being little affected by a long period of use or by use in a highly humid atmosphere, and hence a greatly improved stability relative to the passage of time.

Another object of this invention is to provide a gas sensor comprising a sensor body having an outer periphery formed with a porous layer of silica, alumina or silica-alumina composed of tin oxide, a lanthanide oxide in 0.01–20 mol % of the tin oxide, and a IVa group element oxide in 0.01–20 mol % of the tin oxide, and including a high density of hydroxyl groups on the surface thereof which readily react with organic silicone molecules, thereby to prevent organic silicone molecules from reaching the gas sensor body surface and to restrain changes with the passage of time in the sensitivity of the sensor caused by poisoning, and hence the sensor has a long durability even in bad surroundings.

According to this invention, a uniform mixture forming the gas sensor body and consisting of tin oxide, a lanthanide element oxide and a IVa group element oxide is prepared by one of the following three methods available, i.e. a method in which these components are mixed directly, a method in which a sintered piece is caused to soak a solution of compounds thermally decomposable into substance other than tin oxide and is then calcinated, and a method in which a coprecipitation of hydroxides corresponding to the above three kinds of oxide is obtained from a mixed solution by adjusting the pH and is calcinated.

The porous layer covering the surface of the above gas sensor body may be formed, for example, by turning powder of alumina, silica or the like into a paste, applying the paste to the surface of the sensor body and calcinating it after drying.

Therefore, gas sensors according to this invention not only have excellent poison resistance and durability but also are easy to manufacture which insures invariable quality, and that at low cost. Such sensors are capable of highly reliable gas leakage alarms, and make great contributions toward improving safety at dwelling houses, factories, offices and so forth.

Other objects and advantages of this invention will be apparent from the following description.

DETAILED DESCRIPTION OF THE PREFERRED EMBODIMENTS

First Embodiment

A gas sensor comprises a sintered piece consisting mainly of tin oxide and formed on an alumina base plate to cover a pair of forked platinum electrodes. Each of the electrodes is connected to a lead wire. The base plate includes a platinum heater on a back face thereof.

Examples of method for forming the above sintered piece are described next.

EXAMPLE 1

A predetermined amount of tin oxide ($SnO_2$) is mesured, to which the oxide of a lanthanide element and the oxide of an element included in the periodic group IVa are added in a predetermined ratio. The three components are then mixed one another with water, crushed and kneaded into a paste. Next, the paste is applied between the pair of platinum electrodes formed on the front face of the alumina base plate having the platinum heater on the back face, dried under 80° C. for two hours, and is then calcinated under 800° C. for two hours (This method is hereinafter referred to as the kneading method).

EXAMPLE 2

Tin oxide powder is first kneaded with water to form a paste which is applied between the platinum electrodes on the alumina base plate and allowed to dry as in the foregoing method, and is then presintered under 400° C. for one hour. The presintered piece is caused to soak an aqueous solution of a lanthanide element compound and a compound of element of the group IVa thermally decomposable into oxides, to cause the latter two to be contained in the former in predetermined amounts. The resulting product is dried and is thereafter calcinated under 800° C. for two hours (This method is hereinafter referred to as the soaking method).

EXAMPLE 3

An aqueous solution of a lanthanide element compound and a compound of element of the group IVa as in Example 2 is added in a predetermined amount to an aqueous solution of tin (Sn) compound. When the tin compound is caused to precipitate as hydroxide by adjusting the pH, these additives too are caused to coprecipitate at the same time. Thereafter, the precipitation is separated, dried, and turned into a uniform paste as in Example 2, which is applied between the electrodes on the alumina base plate and, after drying, is calcined under 800° C. for two hours (This method is hereinafter referred to as the coprecipitation method).

PERFORMANCE TEST

Gas sensors comprising the sintered semiconductors prepared according to Example 1 (the kneading method), Example 2 (the soaking) and Example 3 (the coprecipitation method) were maintained in energized, use state for 200 hours, and were made to contact the gases of 1,000 ppm hydrogen, 1,000 ppm methane and 1,000 ppm ethanol to measure the electric resistance in the respective cases, which was regarded as the initial resistance. Thereafter, changes in the gas sensitivity with the passage of time were measured by maintaining the gas sensors in the use state. Measuring results of each gas sensor are shown in Table 1.

As seen from Table 1, stability in relation to the passage of time is markedly improved by the addition of a lanthanide oxide and the like.

It has been confirmed through tests that good results are obtained from the lanthanide oxide and the group IVa element oxide in the range of 0.01–20 mol % with respect to tin oxide.

TABLE 1

| Sample No. | Amounts of additives in $SnO_2$ | | | | $\frac{R \text{ (resistance after 3000 Hrs)}}{R'o \text{ (initial resistance)}}$ | | | | Method of addition |
|---|---|---|---|---|---|---|---|---|---|
| | Lanthanide oxide | mol % | IVa element oxide | mol % | In air containing no gas | In air containing a gas of 1000 ppm | | | |
| | | | | | | $H_2$ | $CH_4$ | $C_2H_5OH$ | |
| 1 | $La_2O_3$ | 0.5 | $ZnO_2$ | 1 | 0.88 | 0.78 | 0.92 | 0.76 | (A) |
| 2 | $La_2O_3$ | 0.5 | $HfO_2$ | 1 | 0.92 | 0.81 | 0.92 | 0.78 | (A) |
| 3 | $CeO_2$ | 0.5 | $ZnO_2$ | 1 | 0.98 | 0.94 | 0.99 | 0.89 | (C) |
| 4 | $CeO_2$ | 0.5 | $ThO_2$ | 1 | 0.97 | 0.92 | 0.98 | 0.92 | (C) |
| 5 | $Nd_2O_3$ | 1 | $HfO_2$ | 2 | 0.95 | 0.84 | 0.96 | 0.84 | (B) |
| 6 | $Sm_2O_3$ | 1 | $ThO_2$ | 2 | 0.94 | 0.86 | 0.98 | 0.82 | (B) |
| 7 | $Dy_2O_3$ | 1 | $ThO_2$ | 2 | 0.96 | 0.90 | 0.98 | 0.86 | (B) |
| 8 | $La_2O_3$ | 2 | $TiO_2$ | 2 | 0.98 | 0.94 | 0.98 | 0.90 | (B) |
| | | | $ThO_2$ | 2 | | | | | |
| 9 | $La_2O_3$ | 2 | $ZrO_2$ | 5 | 0.98 | 0.97 | 0.98 | 0.94 | (A) |
| | $Sm_2O_3$ | 2 | | | | | | | |
| 10 | $CeO_2$ | 2 | $HfO_2$ | 5 | 0.97 | 0.98 | 0.96 | 0.96 | (C) |
| | $Dy_2O_3$ | 2 | $ThO_2$ | 5 | | | | | |
| Blank (without any additive) | | | | | 0.74 | 0.56 | 0.92 | 0.52 | |

Notes:
The symbol (A), (B) and (C) respectively indicate the kneading, the soaking and the coprecipitation

Second Embodiment

The gas sensor comprises a sensor body peripherally coated with a porous layer. This porous layer comprises silica or alumina which is prepared by the wet method, calcinated under low temperature and left standing in the ambient air, and therefore includes more hydroxyl groups on its surface than oxides prepared by other methods such as the dry method.

When organic silicone such as trimethylsilanol, i.e. $(CH_3)_3SiOH$, is adsorbed by the surface of the porous layer such as of silica it reacts with the surface hydroxyl groups. Alumina too has the surface hydroxyl groups likewise reactive with the silanol group. Organic silicone molecules are highly reactive with the surface hydroxyl groups of an oxide, and are taken into the oxide surface to thermally decompose into silica at once, without reaching the inner sensor body. On the other hand, $H_2$, CO, $CH_4$ and other gases do not react at the porous layer but reach the sensor body to be detected.

The formation of the porous layer is described next. Ammoniac water is dripped into an aqueous solution of aluminum nitrate to precipitate aluminum hydroxide. After treating this precipitation to produce boehmite, it is washed, dried and calcinated at 550° C. for five hours to obtain alumina powder. This alumina powder is kneaded with colloidal alumina and water into a mud-like paste. Then the paste is applied in a thickness of about 0.1 mm to the periphery of the sensor body, which is calcinated after drying to obtain the poison resisting gas sensor.

Next, when the gas sensor comprising a catalytic oxidation type sensor body utilizing a palladium catalyst and a porous alumina layer formed thereon is brought into contact with the air conditioning 1.25 percent of methane gas and 10 ppm of trimethylsilanol, the gas sensor provides an output changing with the passage of time. Thus it shows a good poison resistance with sharp contrast to the sensor body without the porous layer which changes with the passage of time.

In the case of the gas sensor according to this invention comprising the sensor body including a 0.4 mm thick sintered layer of tin oxide formed on the insulating base plate attached with the platinum film electrodes, and the porous alumina layer provided peripherally of the sensor body as already described, a contact thereof with the air conditioning 0.4 percent of hydrogen gas and 10 ppm of trimethylsilanol brings about little change with the passage of time on the output of the sensor. The sintered semiconductor sensor, though its mechanism is unclear, increases its sensitivity as poisoned by organic silicone, and the sensor body without the porous layer increases its sensitivity with the passage of time in the presence of organic silicone. But it is markedly restrained according to this invention.

It has been found that, apart from the above alumina powder, like effect is produced by a sintered layer of silica or silica-alumina prepared by treating an aqueous solution of sodium silicate with a cation-exchange resin.

What is claimed is:

1. A gas sensor adapted to detect hydrogen, methane, ethyl alcohol and the like and maintained at about 300° to 450° C. in operation, the gas sensor comprising:
    a sintered piece composed of tin oxide ($SnO_2$), at least one of lanthanide oxides in 0.01–20 mol % of the tin oxide, and at least one of IVa group metal oxides in 0.01–20 mol % of the tin oxide.
2. A gas sensor as defined in claim 1 wherein the lanthanide oxides are contained at about 0.05 to 4 mol % of the tin oxide, and the IVa group metal oxides are contained at about 0.05 to 10 mol % of the tin oxide.
3. A gas sensor as defined in claim 2 wherein the sintered piece comprises a calcinated paste, said paste including a mixture of fine powders of all of said oxides.
4. A gas sensor as defined in claim 2 wherein the sintered piece comprises a presintered piece of tin oxide powder, the presintered piece including the lanthanide oxides and the IVa group metal oxides which are respectively converted from thermally decomposable compounds corresponding thereto.
5. A gas sensor as defined in claim 2 wherein the sintered piece comprises a calcinated coprecipitation of hydroxides of tin, lanthanides and IVa group metal oxides.

* * * * *

UNITED STATES PATENT OFFICE
CERTIFICATE OF CORRECTION

PATENT NO. : 4,592,967
DATED : June 3, 1986
INVENTOR(S) : Koji Komatsu and Sai Sakai It is certified that error appears in the above-identified patent and that said Letters Patent are hereby corrected as shown below:

Change "Filed: February 24, 1984" to "Filed: January 31, 1984".

Signed and Sealed this

Fifteenth Day of September, 1987

Attest:

DONALD J. QUIGG

*Attesting Officer*  *Commissioner of Patents and Trademarks*